(12) United States Patent
Pathria et al.

(10) Patent No.: US 8,639,522 B2
(45) Date of Patent: Jan. 28, 2014

(54) CONSISTENCY MODELING OF HEALTHCARE CLAIMS TO DETECT FRAUD AND ABUSE

(75) Inventors: Anu Kumar Pathria, La Jolla, CA (US); Andrea L. Allmon, San Diego, CA (US); Jean de Traversay, Solana Beach, CA (US); Krassimir G. Ianakiev, San Diego, CA (US); Nallan Suresh, Irvine, CA (US); Michael K. Tyler, San Diego, CA (US)

(73) Assignee: Fair Isaac Corporation, San Jose, CA (US)

( * ) Notice: Subject to any disclaimer, the term of this patent is extended or adjusted under 35 U.S.C. 154(b) by 1319 days.

(21) Appl. No.: 12/104,242

(22) Filed: Apr. 16, 2008

(65) Prior Publication Data

US 2008/0249820 A1 Oct. 9, 2008

Related U.S. Application Data

(63) Continuation of application No. 10/360,858, filed on Feb. 6, 2003, now Pat. No. 7,813,937.

(60) Provisional application No. 60/357,387, filed on Feb. 15, 2002.

(51) Int. Cl.
*G06Q 10/00* (2012.01)
*G06Q 50/00* (2012.01)

(52) U.S. Cl.
USPC .................. 705/2; 705/3; 705/4; 706/21

(58) Field of Classification Search
USPC ............................................. 705/2–4; 706/21
See application file for complete search history.

(56) References Cited

U.S. PATENT DOCUMENTS

| | | | | |
|---|---|---|---|---|
| 6,826,536 | B1 * | 11/2004 | Forman ............................ | 705/4 |
| 7,376,618 | B1 * | 5/2008 | Anderson et al. ............... | 705/38 |
| 7,418,431 | B1 * | 8/2008 | Nies et al. ....................... | 706/21 |
| 2003/0126102 | A1 * | 7/2003 | Borthwick ....................... | 706/21 |

* cited by examiner

*Primary Examiner* — Luke Gilligan
(74) *Attorney, Agent, or Firm* — Mintz, Levin, Cohn, Ferris, Glovsky and Popeo, P.C.

(57) ABSTRACT

Transaction-based behavioral profiling, whereby the entity to be profiled is represented by a stream of transactions, is required in a variety of data mining and predictive modeling applications. An approach is described for assessing inconsistency in the activity of an entity, as a way of detecting fraud and abuse, using service-code information available on each transaction. Inconsistency is based on the concept that certain service-codes naturally co-occur more than do others. An assessment is made of activity consistency looking at the overall activity of an individual entity, as well as looking at the interaction of entities. Several approaches for measuring consistency are provided, including one inspired by latent semantic analysis as used in text analysis. While the description is in the context of fraud detection in healthcare, the techniques are relevant to application in other industries and for purposes other than fraud detection.

22 Claims, 7 Drawing Sheets

CONSISTENCY MODELING OF HEALTHCARE CLAIMS TO DETECT FRAUD AND ABUSE

CROSS REFERENCE TO RELATED APPLICATIONS

This application is a continuation of U.S. patent application Ser. No. 10/360,858, filed on Feb. 6, 2003 which in turn claims the benefit of provisional application 60/357,387, filed Feb. 15, 2002 (the contents of which are hereby fully incorporated). In addition, this application incorporates by reference application Ser. No. 09/606,575, filed on Jun. 28, 2000 entitled "Cascaded Profiles For Multiple Interacting Entities," ("Cascaded Profiles") and application Ser. No. 09/672,142 filed Sep. 27, 2000 entitled "Webstation: Configurable Web-Based Workstation For Reason Driven Data Analysis" ("Webstation").

BACKGROUND

1. Field of the Invention

The invention relates to analysis of healthcare reimbursement claims for fraud and abuse, and more particularly to the use of consistency modeling methodologies to identify potentially fraudulent or abusive activity in healthcare, both by providers and patients.

2. Description of the Related Art

Healthcare fraud continues to be a growing problem in the United States and abroad. According to the Centers for Medicare and Medicaid Services (CMS), fraud schemes range from those perpetrated by individuals acting alone to broad-based activities by institutions or groups of individuals, sometimes employing sophisticated telemarketing and other promotional techniques to lure consumers into serving as the unwitting tools in the schemes. Seldom do perpetrators target only one insurer or either the public or private sector exclusively. Rather, most are found to be simultaneously defrauding public sector victims such as Medicare and private sector victims simultaneously.

According to the Center for Medicare and Medicaid Services (CMS), annual healthcare expenditures in the United States totaled over $1.4 trillion dollars in 2001, and are expected to increase 6.5% a year. Though the amount lost to healthcare fraud and abuse cannot be quantified to the dollar, the general consensus is that a significant percentage is paid to fraudulent or abusive claims. A July 1997 audit of annual Medicare payments by the Inspector General found that approximately 14 percent of Medicare payments (about $23.2 billion) made in fiscal year 1996 were improperly paid, due to fraud, abuse, and the lack of medical documentation to support claims. Many private insurers estimate the proportion of healthcare dollars lost to fraud to be in the range of 3-5%, which amounts to roughly $30-$50 billion annually. It is widely accepted that losses due to fraud and abuse are an enormous drain on both the public and private healthcare systems.

In Medicare, the most common forms of provider fraud include:

Billing for services not furnished

Misrepresenting the diagnosis to justify payment

Soliciting, offering, or receiving a kickback

Unbundling or "exploding" charges

Falsifying certificates of medical necessity, plans of treatment, and medical records to justify payment Billing for a service not furnished as billed; i.e., upcoding.

In addition to provider fraud, there is also client abuse, arising from such activities as card-sharing, acting in collusion with a provider for kickbacks, etc.

One of the ways in which fraud can be evaluated in the medical care setting, and indeed many other transactional environments, is by modeling interactions between different entities such as individuals, organizations or groups. In such cases, the activity related to the problem at hand is largely described by a body of transaction data (historical and/or ongoing) that captures the behaviors, including interactions, of the relevant entities. A few sample settings along with the corresponding transaction data and related entities are described below in Table 1.

TABLE 1

| Problem/Setting | Transactions | Entities |
| --- | --- | --- |
| Healthcare fraud and abuse detection | Claims (inpatient and outpatient) | Client (Patient), Doctor, Hospital, Pharmacy, Lab |
| Credit Card fraud detection | Purchases, Payments, Non-monetary transactions | Account holder, Merchant, Credit Card issuer |
| Bank Checking System | Check processing transactions | Account holder, Bank, Teller |
| Food Stamp fraud detection | Food Stamp transactions | Retailer, Client (Recipient) |
| Worker's Compensation fraud detection | Injury report, Payments, Medical Services | Claimant, Provider |

In each of these settings, the common phenomenon is the fact that the encounters between the different entities are captured in the form of the associated transactions.

An entity is an operational unit within a given setting, application or environment and represents objects that interact within that setting, application or environment. The members of an entity are generally objects of a similar type. Different entities interact with each other and their interactions are encapsulated in the transaction data corresponding to that application. Thus, examples of entities in a healthcare setting are clients, providers (this includes doctors, hospitals, pharmacies, etc.), clients' families, etc., and their interactions are captured in the claims data; i.e. the interaction of a healthcare provider and a patient is captured in a claim by the provider for reimbursement. In the credit card environment, the interacting entities are account holders, merchants, credit card issuers, and the like and their interactions are captured through different types of transactions such as purchases and payments.

Usually, entities correspond to individuals or organizations that are part of the setting, as the examples above illustrate. However, more abstract entities characterizing a transaction may also be defined. Examples include procedure codes (describing the type of healthcare service rendered), resource, utilization groups (RUC's), diagnosis-related groups (DRG's), and SIC codes (Standard Industry Codes), etc.

A member of an entity is an individual instance of the entity. For example, a specific doctor is a member of the healthcare provider entity; a particular grocery store is a member of the credit card merchant entity; and so on.

As noted above, a transaction captures information associated with an interaction between a group of entities. A transaction may initially arise between two entities (e.g. a doctor and a patient) and then be processed by still other entities (e.g. a pharmacy providing a prescription and a laboratory providing a lab test required by the doctor). Different types of transactions will typically capture different types of interactions or interactions between different groups of entities. For example in the credit card setting, a purchase transaction captures the interaction between the cardholder and the merchant, while a payment transaction encapsulates the information regarding the payments made by a cardholder to the credit card issuer. Similarly, in healthcare, an outpatient claim represents the service received by a client (i.e. patient) from a provider as part of an office or home visit, while an inpatient claim encodes data regarding a patients stay at a hospital or another facility.

In the past, profiles have been created for individual entities and used to develop statistical models based solely on the profiles of the individual entities. For example, U.S. Pat. No. 5,819,226 discloses, among other things, the use of profiles of individual credit card account holders for modeling credit card fraud by such individuals. While this approach is useful for particular applications, in other applications it is desirable to understand the complex interactions between different entities. For example, in order to determine whether there is fraudulent activity by a healthcare provider, it is important to view the provider's activity not just in a vacuum, but also in relation to the activities of all other similar providers (e.g. providers having the same specialty), as well as in the context of the patients on whom the services are performed. Accordingly, profiles based only on transactions of individual members of the entity are insufficient to capture these rich interactions between entities in a manner that yields statistically useful information for modeling the interactions between entities.

Because of the high cost of healthcare fraud, profiling provider activity on the basis of medical claims sent for reimbursement in order to detect fraud and abuse is of significant importance to healthcare payers. The provider can generate extra income by, for example, exaggerating service performed, delivering unnecessary services, submitting claims for services never rendered, etc.

Accordingly, there is a need for a system and method to detect fraud in the healthcare industry by evaluating the legitimacy of medical claims.

SUMMARY OF THE INVENTION

Introduction

The present invention provides a system and method for assessing the consistency of services provided to or received by entities, such as patients, facilities, physicians, and the like. Thus, the consistency of services delivered, or more precisely the lack of consistency delivered to a set of patients by one or more healthcare providers can be assessed to identify potentially fraudulent or abusive practices. Additionally, false positives can be reduced by appropriately considering case-mix when assessing a provider's activity.

A set of services is "consistent" if the services tend to occur together on a single entity that is, for a patient (or, more generally, a client) having a first service performed, in the absence of fraud or deception there is a greater than average likelihood that a second service would also be performed. The present invention includes a methodology for assessing the consistency of activity at the client level (i.e. how consistent is the client's set of services), and at the provider/client level (i.e. how consistent is the provider's activity on the client given all other services performed on the client). This assessment of consistency can then be aggregated across all clients of a provider to come up with an overall assessment of the consistency of the provider's activity in the context of the clients on whom the services are performed. In addition, it can lead to the discovery of abuse at the client or provider/client level itself.

Such analysis detects fraud and abuse that would otherwise go unnoticed. No matter how careful or subtle the provider is, the fraudulent or abusive provider typically will not know about all other activity (e.g., procedures, admissions, prescriptions, etc.) occurring on the client, and hence is likely to do something not entirely consistent with other activity seen on the client. By assessing the consistency of the provider with respect to all of its clients, an accurate overall picture can be obtained of the appropriateness of the provider's activity. This allows for the identification of providers who are systematically billing inappropriately for services.

This consistency modeling approach not only increases detection, but also reduces false-positives, i.e. mislabeling of genuine activity as fraudulent. Providers often claim, when questioned about fraud or abuse, that while their overall service-code mix may be different from other providers, it is because their patient mix is different. Indeed, false-positives in conventional fraud and abuse detection systems often do correspond to hyper-specialists and other providers whose clientele is atypical. The techniques used by the present invention provide a sophisticated approach to the issue of "case-mix adjustment", that is, adjusting the assessment of the provider's activity based on the patient mix. Hence, a determination may be made that a certain provider's activity is unusual if the patient mix is ignored, but in the context of the clients being serviced it is perfectly reasonable.

Explication

A transaction in the healthcare setting is a medical claim submitted to the payer for reimbursement to the provider for services rendered. A medical claim typically includes data such as date of service, performing provider (as well as billing and referring providers), amount paid, patient ID, service-code, diagnosis codes, etc. Typical service coding schemes include CPT's (for physicians), DRG's (facilities), RUG's (nursing homes), etc. For ease of understanding, each of these is referred to herein as a service code. Note that diagnoses can also be considered "service-codes"; indeed, the present invention applies to any categorical code that is associated with each transaction. Certain services naturally go together in an associated episode of care (e.g. MRI, knee surgery, physical therapy), while others are less likely to occur on a given individual (e.g. multiple appendectomies; vasectomy followed by child-birth; dental braces and a physical). The present invention offers a methodology to assess how consistent a provider's services performed on a client are, given all other services performed on the client. In addition, the overall consistency of the client's or the provider's activity can also be assessed.

Consistency is based on co-occurrence. Statistical analysis of actual claims data reveals how common it is for a set of services to co-occur on a given client. (Services occur "on" a client if they are performed on, for, or on behalf of the client.) The present invention includes three different techniques for assessing consistency.

The first technique looks for unusual situations involving multiple occurrences of the same service on the same client. This analysis flags unlikely events like multiple appendectomies, where a given procedure should not logically be repeated-humans have only one appendix. Also flagged by this technique are those procedures that are highly unlikely to occur within a given time of a preceding service. For example, it is highly unlikely for a patient to be given two flu shots during the same flu season.

The second technique assesses, for each pair of services occurring on an entity, the likelihood of this service pair co-occuring. For example, historical data might suggest that patients who are treated for herniated discs tend to have MRIs. Conversely, patients given a polio vaccine (normally performed on very young patients) are not likely to also be treated for hair loss (normally performed on older patients), and tubal ligations are not generally followed by childbirth.

The third approach, which is the most holistic and sophisticated, is based on a vector space modeling of service co-occurrence, in which the performed service codes are represented in a vector space derived from the statistical distribution of service codes in reimbursement claims. The services associated with each client, provider, or client/provider entity can be represented by a vector in this space and compared with vectors representing any other entity (e.g., other patients, providers, patient/providers, or sets of services).

This third approach is inspired in part by Latent Semantic Analysis (LSA) used for free-text analysis. In text analysis, a document can be thought of as a "bag of words" represented by a high-dimensional vector, where each component corresponds to the presence of a particular term (e.g. a word) in the document. A co-occurrence document-by-term matrix combines such vectors across all documents in a corpus. These documents can be mapped from term-space to a reduced dimensionality via singular-value-decomposition (SVD) of the original matrix, that is, by performing a Principal Component Analysis. The reduced dimensional space maintains as much information/meaning as possible of the original document taking advantage of the natural co-occurrence of various services to do so. Two documents with similar meaning should map to a similar reduced-space representation. This reduced dimensionality representation is useful for space-saving reasons, but it is also valuable for classification and retrieval based on meaning as synonymous terms/concepts map to similar points. See, for example, Konstantinos Diamantaras and S. Y. Kung, "Principal Component Neural Networks: Theory and Applications", in the series "Adaptive and Learning Systems for Signal Processing, Communications, and Control", John Wiley & Sons, February 1996, incorporated by reference herein. As such, one can think of the mapping as being from original space to concept/meaning space. In addition to SVD, various non-linear techniques (e.g. neural network based techniques) also exist for creating such a mapping.

In the healthcare environment, "terms" are service-codes and "documents" are the set of services associated with a given individual. Given this mapping, LSA type techniques can then be applied to construct the vector space for the service codes, and dimensionality reduction can be performed. A client vector can be created for each client based upon the underlying service code vectors. This provides a vector that represents the services provided to a client over a time period. It can then be determined whether a particular service or set of services by a provider for a client is consistent with the services previously rendered for the client by comparing the client vector with a vector representing the services codes in question. A measure of the distance between the vectors indicates whether the services are consistent. Comparisons can also be made between an original vector prior to dimensionality reduction and a reconstructed vector to determine the consistency. Where the reconstructed vector is significantly different from the original vector an inference can be made that the services expressed by the original vector are inconsistent.

The present invention has application beyond healthcare fraud/abuse detection. There is value to fraud/abuse detection in other industries, for example auto warranty over-servicing: the analogy with healthcare is that the auto-manufacturer is the payer, the dealer is the service provider, and the car-owner is the client. There is also value beyond fraud/abuse, as the reduced-space representation can be used for clustering providers or clients into peer-groups, classification (e.g. assigning provider specialty), forecasting quantities like utilization, etc.

The figures depict a preferred embodiment of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF PREFERRED EMBODIMENTS

I. Conceptual Flow

Figure 1:
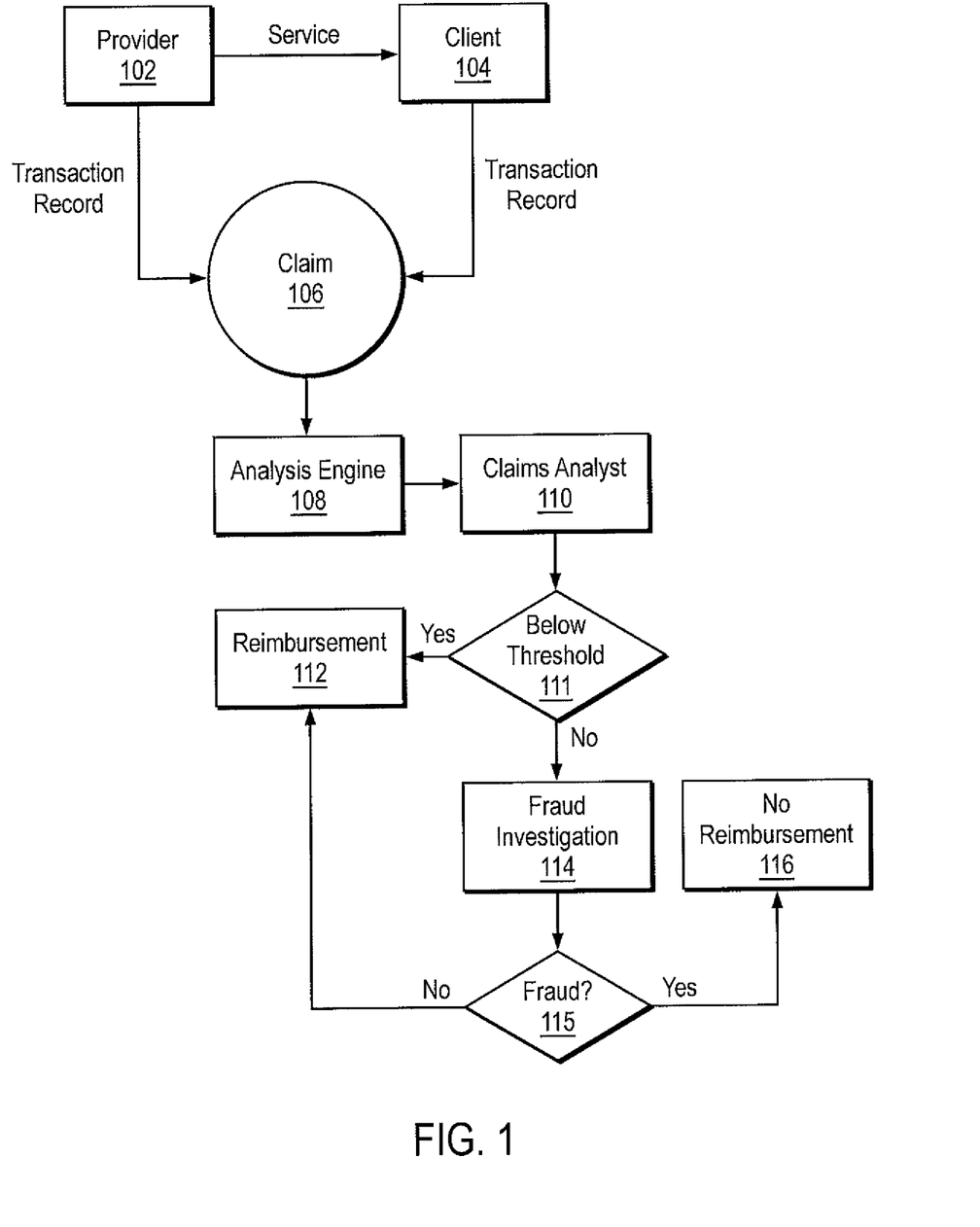
FIG. 1 is a high level illustration of the flow of data in accordance with an embodiment of the present invention.

Referring now to FIG. 1, there is shown a high level illustration of the flow of data in accordance with an embodiment of the present invention. Provider 102 provides a service to client 104. A transaction record of the service is submitted as claim 106 to, e.g., an insurance company for reimbursement. Analysis engine 108 scores the claim to determine the likelihood that the claim is fraudulent. The claim and score are provided to a claims analyst 110. If the score is below a certain threshold 111, the claim is reimbursed 112 or otherwise disposed of without investigation. If the score is above the threshold 111, the claim, the client, and/or the provider are further investigated for fraudulent activity 114. Depending on the outcome 115 of the investigation, the claim is either reimbursed 112, or not 116.

II. System Architecture

Figure 2:
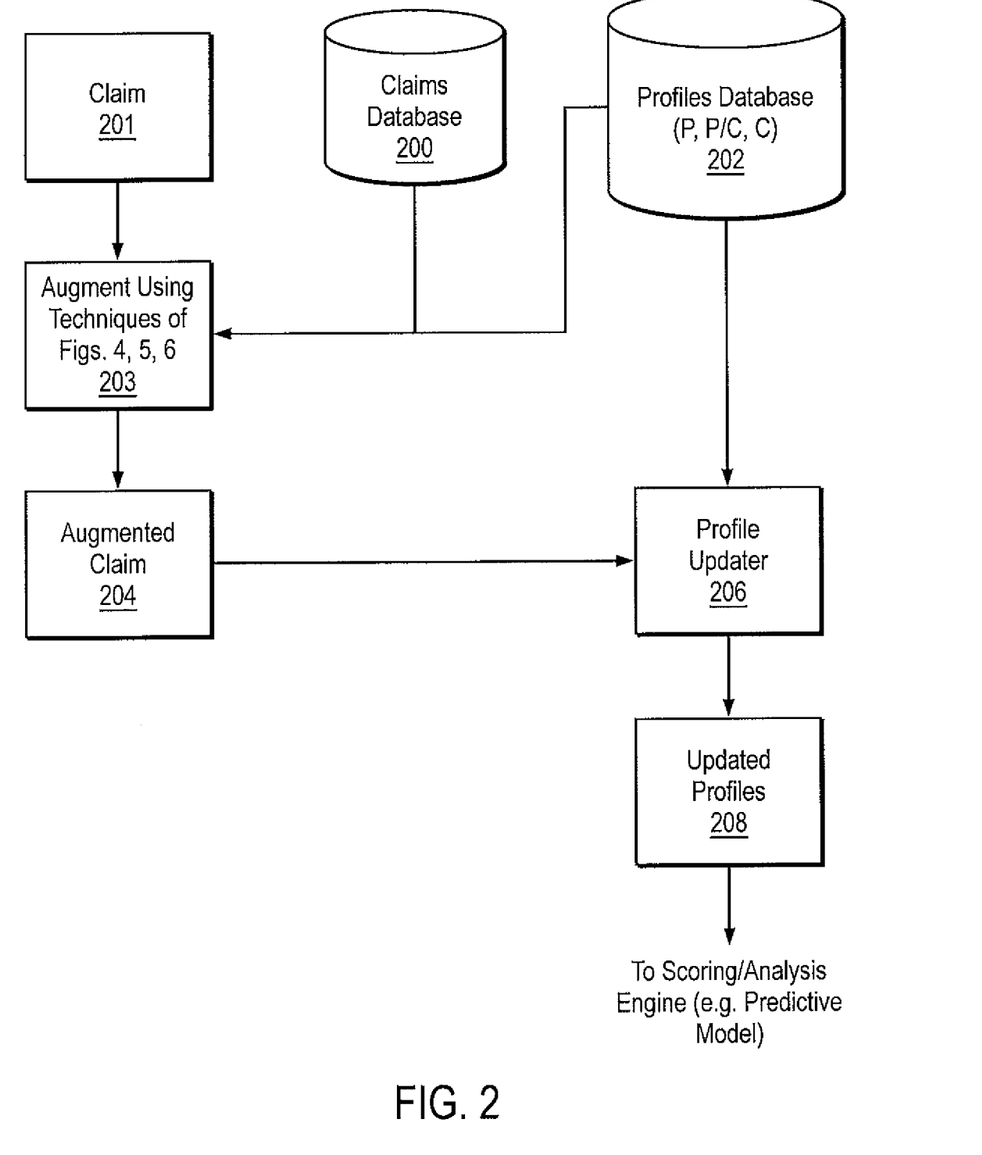
FIG. 2 is an illustration of one embodiment of a system architecture for practicing the present invention.

Referring now to FIG. 2 there is shown an embodiment of a system architecture for practicing the present invention.

A claims database 200 usually found in the healthcare line of insurance either follows the professional services standard format (HCFA1500 form), the facilities standard format (UB92 form) or the dental standard format (Dental ADA form). These standard formats are currently (as of the year 2002) being transitioned under HIPAA to new national standards: the ASC X12N 837—Professional, the ASC X12N 837—Institutional, and ASC X12N 837—Dental, respectively. The particular formats and contents for establishing these consistency models are expected to vary for different types of insurance (and possibly even for different insurers within the same line of insurance) and are not material to the invention.

As noted, a medical claim typically includes data such as date of service, performing provider (as well as billing and referring providers), amount paid, patient ID, service-code, diagnosis codes, etc.

Profiles database 202 includes profiles of providers, clients, and provider/client pairs. Profiles may be created in a variety of ways. For a description of a cascaded profiling structure, see related application Ser. No. 09/606,575.

Claims 201 are evaluated 203 against historical data as described below with reference to FIGS. 4, 5, and 6, and an augmented claim record 204 is derived, which has associated with it a measure of the consistency (or inconsistency) of the claim and/or provider associated with the claim. The augmented claim records are combined with the profiles 202 to update the profiles according to profile updater 206. Updated profiles 208 are sent to a scoring/analysis engine (e.g., a predictive model) so that a decision can be made whether to investigate suspicious activity, either at the claim, client, or provider level.

III. Functional Operations

The Setting

A set of transactions can be used to profile entities represented in each transaction. Each transaction has at least one service-code and at least one entity associated with the claim. In healthcare, there are often multiple codes (e.g., CPT codes for procedures, and ICD9 codes for diagnoses), and there are at least two associated entities (provider and patient). The more general term "client" is used herein in lieu of "patient". An entity is represented by the set of service-codes on the claims with which it is associated.

The present invention addresses two related issues in healthcare fraud detection:

1. How internally consistent is the overall activity associated with a given entity. That is, how consistent is the full set of procedures performed on the client?
2. How consistent is a subset of an entity's activity in the context of everything else associated with that entity. For example, how consistent is a particular provider's activity on a patient in the context of everything else occurring on that client?

The consistency assessments can be used in many ways. For example, unusual clients or suspicious provider/client interactions can be identified. In the healthcare fraud detection setting, because any individual unusual client may not suggest any wrong-doing, transactions can be rolled up across all clients to see if there is a pattern of unusual activity for a provider. For example, using a cascaded profiling structure such as that described in related application Ser. No. 09/606, 575, client and provider/client consistency assessments can be rolled up to assess overall consistency of the provider's clients, and in particular how consistent the provider's servicing is in the context of other services performed on each client.

Three approaches are described below, each of which has its own set of merits and is of increasing complexity, to measure service activity consistency. The third approach offers the most sophisticated and holistic methodology.

Approach A: Repeated Services

One approach is to examine how suspicious a given claim's service code is in terms of repeat activity; that is, how unusual is it to repeat this service on the same individual within a given time period? Some procedures, such as an appendectomy, should never occur more than once. Other procedures are unusual when they occur too close together in time, e.g., having two flu shots within 1 year.

Figure 3:
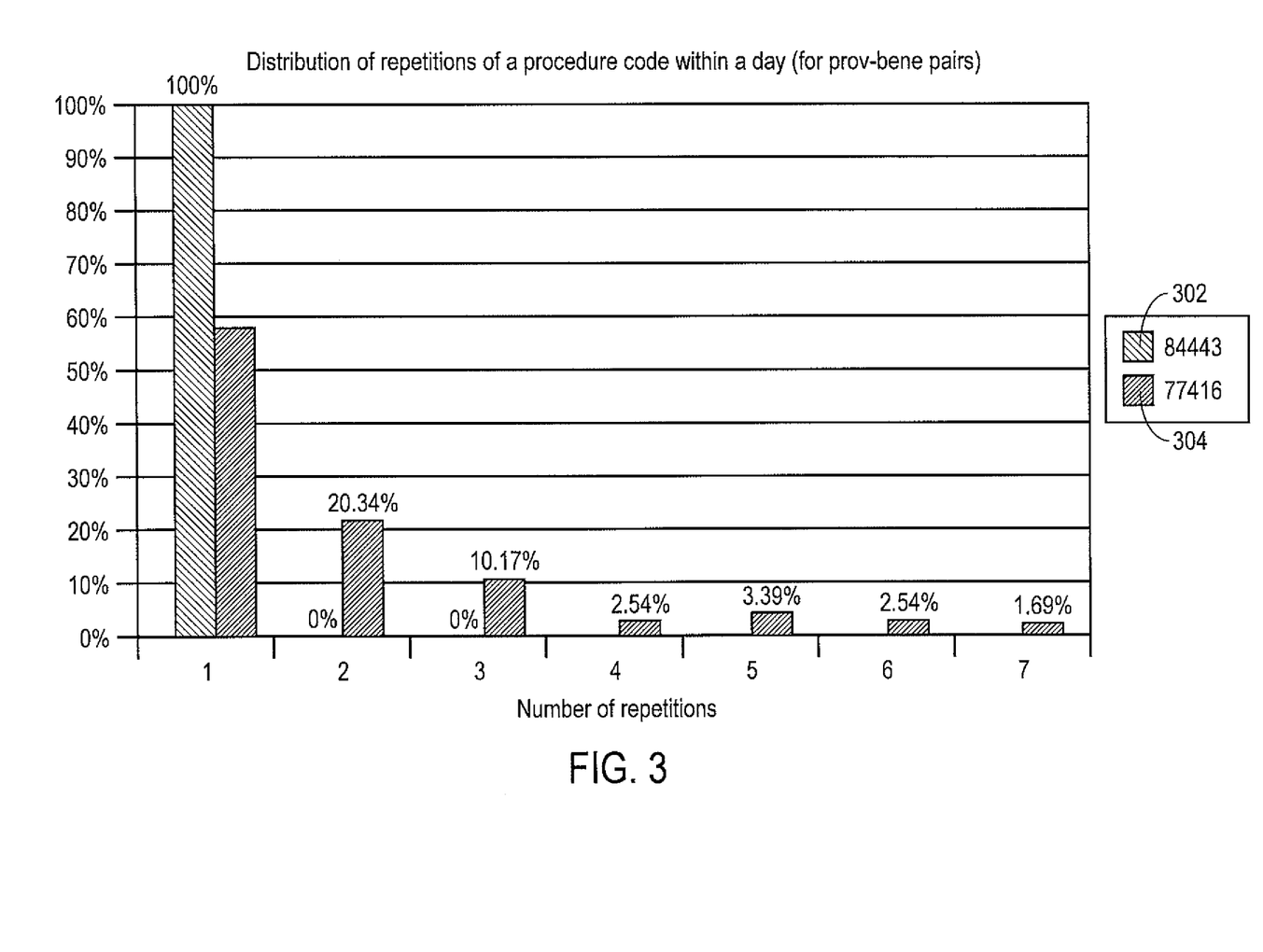
FIG. 3 shows two histograms for each of two different typical procedures in accordance with an embodiment of the present invention.

FIG. 3 shows two histograms 302, 304, for each of two different procedures. Each histogram shows, for patients receiving the procedure, how many of that procedure they typically get on that day. So, seeing multiple instances of CPT 77416 ("radiation treatment delivery") 304 on a given client on a given day is not nearly as unusual it is for CPT 84443 ("thyroid stimulating hormone") 302: about 40% of clients receiving CPT 77416 actual receive multiple instances on the same day, while essentially 0% of those receiving CPT 77416 do.

A table is constructed using historical claims data that characterizes typical client activity for each service-code. There can be multiple statistics for each service-code, each entry representing a service-code S and time period T; the entry is a measure of how unusual it is for a client receiving service S to receive another instance of the same service S within time-period T. For example, the entry can represent the fraction of clients receiving S that do not receive another S within time period T.

This table is used to monitor claims activity. In one embodiment, each claim is assigned a value corresponding to the table entry representing the service-code on the claim and the time-delta between the current claim and the client's most recent claim with the same service-code. A default "unusualness" value, e.g., 0, is assigned if no previous instance with the same client/service-code instance exists. For example, in Table 1 below, each row represents a procedure code, and each column represents how unlikely it is for the procedure to re-occur within a specific time frame (0 days, 7 days, 30 days, 200 days, and 400 days, respectively).

TABLE 1

| Procedure Code | p_0 | p_7 | p_30 | p_200 | p_400 |
| --- | --- | --- | --- | --- | --- |
| E1390 | 0.987 | 0.974 | 0.590 | 0.148 | 0.114 |
| D7240 | 0.552 | 0.551 | 0.550 | 0.550 | 0.519 |
| B4035 | 0.956 | 0.406 | 0.275 | 0.130 | 0.103 |
| A7003 | 0.988 | 0.982 | 0.859 | 0.507 | 0.449 |
| 99397 | 0.977 | 0.976 | 0.973 | 0.965 | 0.850 |
| 99354 | 0.971 | 0.922 | 0.825 | 0.693 | 0.605 |
| 00142 | 0.836 | 0.825 | 0.783 | 0.737 | 0.651 |
| 20550 | 0.758 | 0.703 | 0.594 | 0.467 | 0.411 |
| 30520 | 0.604 | 0.598 | 0.596 | 0.592 | 0.532 |
| 43239 | 0.865 | 0.862 | 0.856 | 0.811 | 0.725 |
| 59025 | 0.918 | 0.431 | 0.343 | 0.326 | 0.281 |
| 66984 | 0.494 | 0.464 | 0.406 | 0.347 | 0.307 |
| 67210 | 0.969 | 0.929 | 0.844 | 0.697 | 0.602 |
| 69210 | 0.980 | 0.962 | 0.945 | 0.864 | 0.769 |
| 73510 | 0.924 | 0.884 | 0.807 | 0.658 | 0.575 |
| 74230 | 0.982 | 0.958 | 0.877 | 0.802 | 0.705 |
| 76075 | 0.955 | 0.953 | 0.952 | 0.949 | 0.876 |
| 81003 | 0.984 | 0.961 | 0.913 | 0.788 | 0.709 |
| 82270 | 0.981 | 0.956 | 0.941 | 0.901 | 0.814 |
| 82746 | 0.981 | 0.976 | 0.966 | 0.912 | 0.837 |
| 82784 | 0.764 | 0.752 | 0.676 | 0.518 | 0.460 |
| 84436 | 0.986 | 0.983 | 0.970 | 0.861 | 0.808 |
| 88342 | 0.751 | 0.726 | 0.685 | 0.640 | 0.571 |
| 90807 | 0.986 | 0.744 | 0.330 | 0.134 | 0.109 |
| 92004 | 0.987 | 0.985 | 0.981 | 0.969 | 0.872 |
| 92012 | 0.991 | 0.960 | 0.887 | 0.614 | 0.497 |
| 92557 | 0.982 | 0.977 | 0.954 | 0.902 | 0.822 |

TABLE 1-continued

| Procedure Code | p_0 | p_7 | p_30 | p_200 | p_400 |
|---|---|---|---|---|---|
| 95115 | 0.990 | 0.549 | 0.107 | 0.033 | 0.025 |

Thus, historically for clients receiving service "84436", 98.3% of the time the next occurrence of that service for the client is more than 7 days later.

Figure 4:
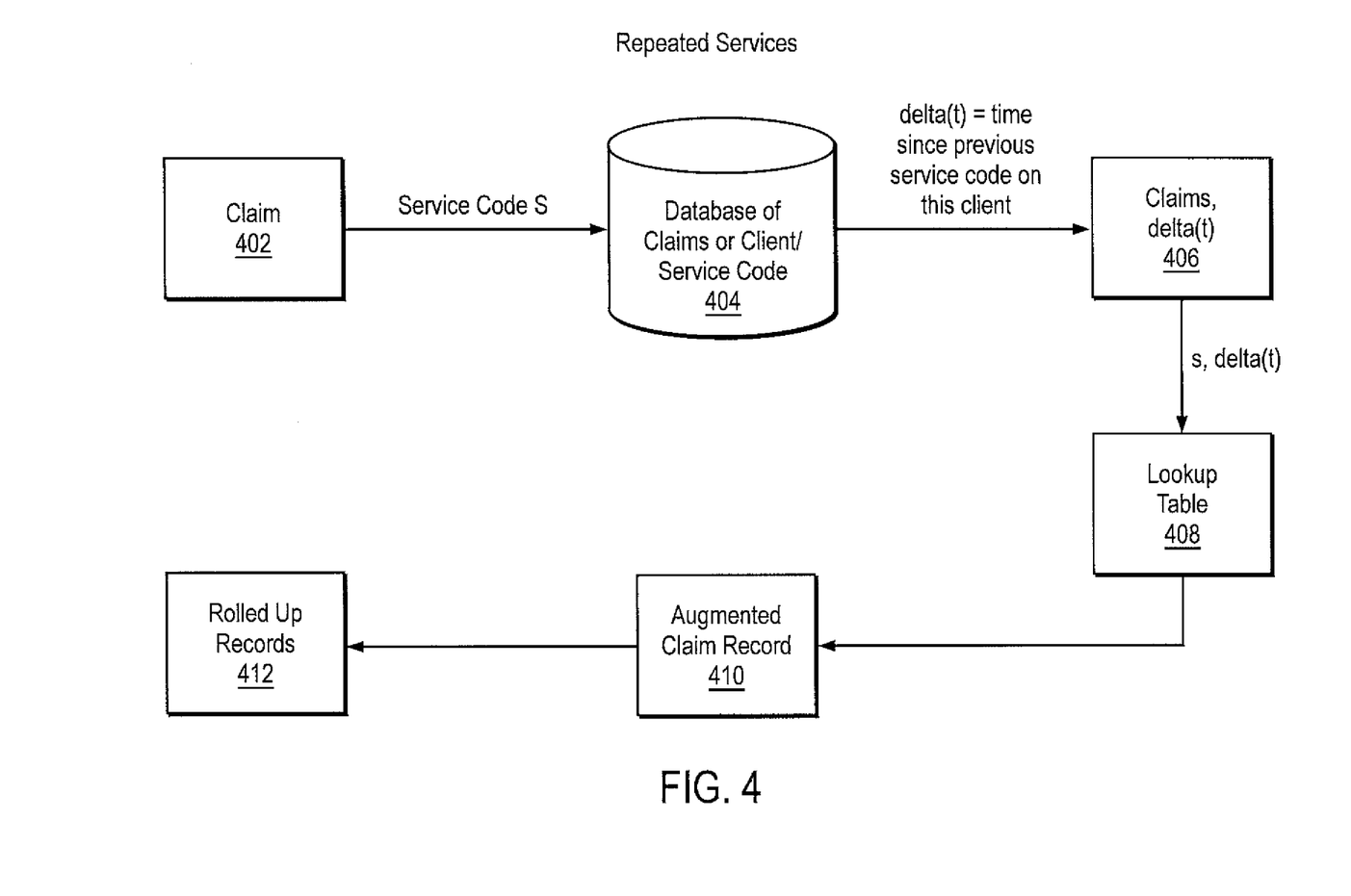
FIG. 4 is a flowgraph of the repeated service analysis methodology in accordance with an embodiment of the present invention.

Referring now to FIG. 4 there is shown a data flow diagram of the repeated services methodology just described. Claims 402 are stored in a claims database 404. In an alternative embodiment, database 404 contains client/service code information extracted from claims. From the claim 402 and the records in the claims database 404, it can be determined how long it has been since the client's last instance of the same service code. This claim/time pairing 406 is compared against values in a lookup table 408 such as Table 1, illustrated above, to determine a score (i.e. a level of suspicion) associated with the claim. The claim record is updated to include this score, and form an augmented claim record 410.

In one embodiment, this augmented claim record is rolled up to a higher-level entity of interest 412, e.g., Provider/Service-Code, to check for abuse at that entity level, i.e. to observe whether there is a broad pattern of unusual repeat-service activity. In one embodiment, rolling up can be as simple as averaging over relevant claims, while in another embodiment it is as sophisticated as the cascaded profile infrastructure, for example as described in related application Ser. No. 09/606,575. In the case of the cascaded profiling infrastructure, for example, an initial rollup to intermediate entities (e.g. Provider/Service-Code, Provider/Client, etc.) can be performed, and these entities are eventually rolled up to the Provider level.

While this analysis can pinpoint areas of abuse with high-precision, it captures only a specific kind of fraud-repeating the same service on the same individual. Thus, most fraud is likely to go undetected if this is the only technique that is utilized.

Approach B: Pair-wise Co-occurrence

A second and broader approach is to consider not only the repetition of an individual procedure, but to assess how natural it is for any pair of procedures to co-occur on a given client. For example, "knee surgery" and "physical therapy" may commonly appear on the same client (that is, such procedures tend to co-occur), but "dental braces" and a "full physical" tend not to appear for the same individual (the former tends to occur on younger clients while latter tends to occur on middle-aged or older clients).

Mathematically, for two procedures $s1$ and $s2$, let $P(s1 \text{ AND } s2)$ represent the joint probability of both occurring on a single client, $P(s1)$ the probability of $s1$ occurring on the client, and $P(s2)$ the probability of $s2$ occurring on the client. These probabilities can be estimated by the frequency of each event in the historical claims data.

If $s1$ and $s2$ tend to occur independently of each other on any given client (that is, the occurrence of one procedure neither increases nor decreases the likelihood that the other will occur), we can expect $P(s1 \text{ AND } s2)$ to approximately equal $P(s1)*P(s2)$. The more the joint probability exceeds the product of the individual probabilities, the more the procedures tend to co-occur; conversely, the more the product of individual probabilities exceeds the joint probability, the more unlikely it is for the two to co-occur on the same client.

This concept can be used to construct an "inconsistency metric", $C(s1,s2)$, which measures how unusual it is for the two procedures $s1$ and $s2$ to co-occur. An example of such a metric is the ratio of the product of their independent probabilities to their joint probability, i.e. $P(s1)*P(s2)$ to $P(s1 \text{ AND } s2)$.

This measure can be used as follows to assess how inconsistent a given service-code $s1$ is against a set of services 52, and ultimately how consistent a set of services S1 is with S2:
1. For each service-code $s2$ in 52, calculate the inconsistency metric $C(s1,s2)$.
2. Roll-up $C(s1,s2)$ across all such $s2$ to come up with a service-code-set inconsistency measure $C(s1,S2)$. This roll-up value can be an "average", a "maximum", or any of a number of other statistics.
3. To compare a set of services S1 against a set S2, aggregate $C(s1,S2)$ across all $s1$ in S1 (again, the aggregation can be any reasonable statistics, such as max, average, etc.).

Figure 5:
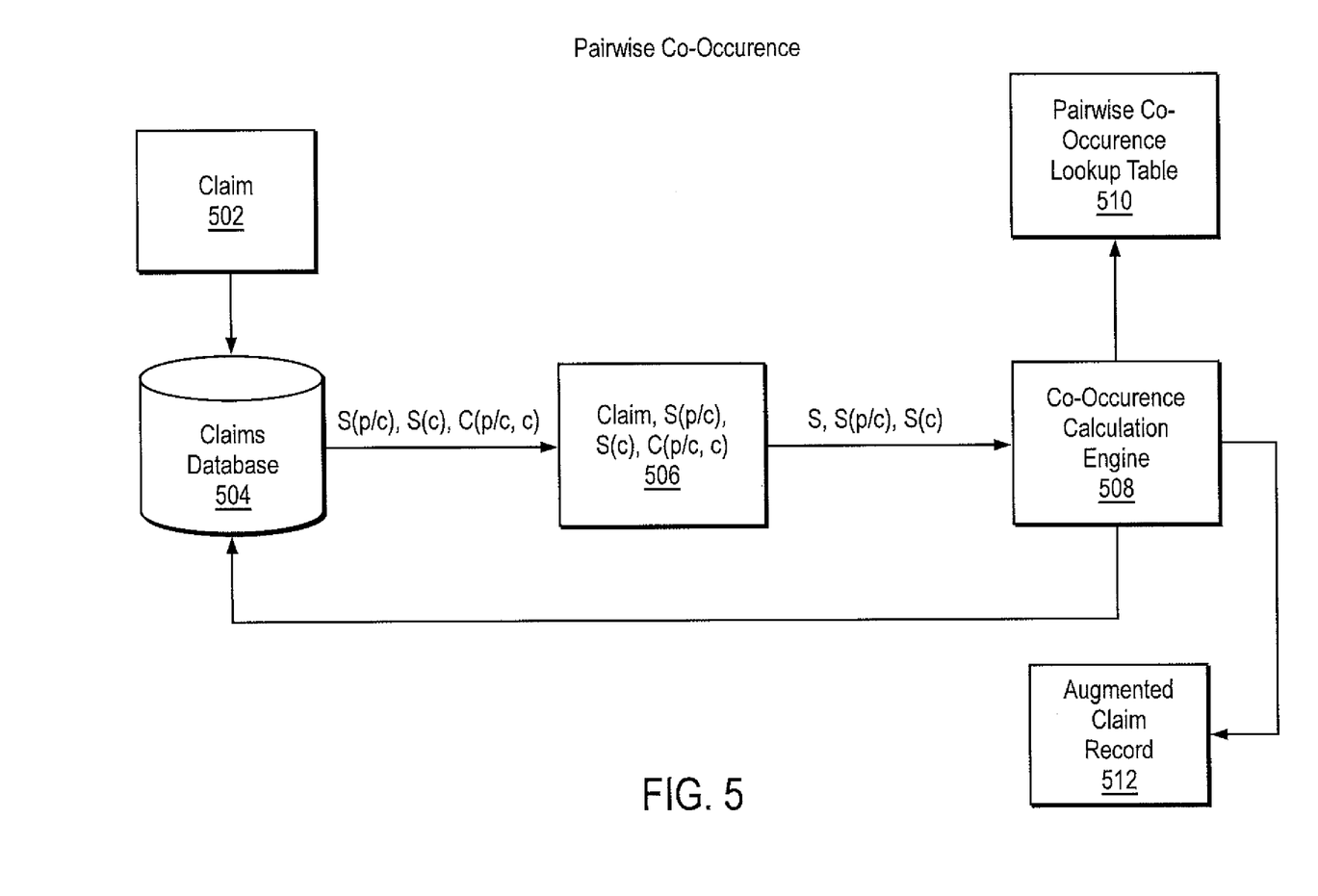
FIG. 5 is a flowgraph of the pair-wise co-occurrence analysis methodology in accordance with an embodiment of the present invention.

Referring now to FIG. 5 there is shown a data flow diagram of the pair-wise co-occurrence methodology just described. Historical claims 502 are stored in a claims database 504. When a new claim comes in, the historical claims data for the client (which in one embodiment is raw claims data, and in another embodiment includes sets of procedures) is culled from the database. In one embodiment all procedures for the client that were performed by the provider of the current claim are excluded from analysis, and in an alternative embodiment they are included, depending on the analysis desired. In a preferred embodiment, data 506 culled from the database includes all services by this provider on this client, all services on this client; and historical values of the consistency between the provider/client and the client as a whole. The current transaction is analyzed by co-occurrence engine 508 against the historical data 506 extracted from the database, and using the co-occurrence values from lookup table 510. Note that the values of the lookup table may be static or dynamically updated. The engine outputs a score indicating, as described earlier, how consistent the current transaction is with all transactions for the client, and how consistent it is with all of that provider's services on the client. The current transaction is added to the database 504 and an augmented claim record 512 is also created as described above with reference to FIG. 4.

The foregoing describes a general process for determination of inconsistency based on the pair-wise assessments. The application can vary, as the examples below illustrate:

In looking for consistency in what a provider is doing on a client in the context of all other service codes associated with that client, then S1 can be the set of services performed by the provider on that client, while S2 is the entire set of services performed on the client excluding what the provider in question has done.

To find internal consistency in a client's activity, S1 and S2 may correspond to the same set of service-codes.

As indicated above, these measures can then be rolled up to the provider level (across all clients) if appropriate.

Approach C: Dimensionality Reduction

A third approach to assessing consistency involves looking at all services performed on an entity simultaneously. As noted earlier this approach is inspired by vector space approaches to text retrieval and in particular latent semantic analysis (LSA) used to understand text documents.

In information retrieval or document classification settings, a text document is often treated as a "bag of words". The objective is to map each "bag of words" to a relatively small, fixed-dimensional space such that documents with similar meaning map to nearby points in this space. A mapping with such characteristics is very useful: First, being able to map any document to a fixed-dimensional representation is important from a memory usage perspective. Second, documents using different terms (words) but having similar meaning (e.g. containing synonyms) are mapped to nearby points and, conversely, documents that share some terms but have very different meanings are represented by points in space that are not nearby. These qualities allow for retrieval and classification systems far more effective than those based on keyword or rule-based criteria. As such, this space can be thought of as a compact "concept-space". The particular choice of reduced-space dimensionality depends on the application and empirical results. Information retrieval using latent semantic structure is conventionally known, and is described further, e.g., in U.S. Pat. No. 4,839,853.

In a similar manner, the nature of illness and pattern of care of a patient or the area of specialty of a provider can be characterized by representing the set of service-codes associated with an entity in a fixed dimensional concept space. Service-codes are the "words", and a "document" is composed of the service-codes that occur for a given individual. Sets of services for similar individuals/illnesses/practices can be expected to have similar representations. For a particular client with a particular illness, the service-codes associated with that client should map to nearby points in the reduced dimension space, while a service-code not associated with the particular illness may map to a distant point.

In a preferred embodiment, a mapping from a set of service-codes to the "concept-space" representation is constructed using historical claims data. A vector is associated with each client, where each vector has dimensionality equal to the number of distinct service-codes, such that every component corresponds to activity associated with a particular service-code. In one embodiment, each vector component is a 0/1 value, indicating whether the service was performed on the client. In an alternative embodiment, each vector component is a count indicating frequency of the procedure. The vectors may be normalized (e.g., scaled to become unit vectors) or not. The data for the vector components is obtained by analysis of all of the claims for each client in a given time period. It is desirable to define a mapping from this original space to a reduced fixed-dimensional space such that as much information as possible is maintained about the original vector space, so that the original vector can be best reconstructed from the compressed representation. Recognition of the fact that certain service-codes tend to co-occur enables this mapping to be designed effectively, minimizing information loss.

Mathematically, we wish to map each point in the original space to a point on a lower-dimensional space that allows us to best reconstruct the original vector. A variety of conventional techniques exist to develop such a mapping, including the following:

A Cottrell-Munro-Zipser compression neural network, conventionally known, and sometimes referred to as an "identity net" or "compression net", can be trained. The system is trained by presenting input/output pairs of vectors, where each pair corresponds to a client and each vector in the pair is identical, namely to the original vector describing service-code activity. Once the network is trained, a vector's reduced dimensionality representation corresponds to the values produced in the middle (hidden) layer when passing the original vector through the network. The output of the network is an attempt to reconstruct the original vector from the reduced dimensionality (i.e. hidden layer) representation. For additional information about Cottrell-Munro-Zipser compression neural networks, see G. W. Cottrell, P. W. Munro, and D. Zipser, "Image compression by backpropagation: a demonstration of extensional programming," in Advances in Cognitive Sciences (N. E. Sharkey, ed.), vol 2, Norwood (N.J.): Abbex, 1988.

If the reduced space is restricted to be a hyper-plane, the above approach corresponds to performing a Principal Component Analysis. The same effect can be achieved analytically. Consider the matrix M made up of the (column) vectors in the original space, describing each client's service-code activity. M is referred to as a co-occurrence matrix, as it indicates which service-codes co-occur for the same individual: rows correspond to service-codes, and service-codes that tend to co-occur will have similar row vectors. By performing a "singular value decomposition" (SVD) on this co-occurrence matrix, a new matrix is produced that allows a mapping from any vector in the original space to the reduced space. Furthermore, a reduced-space vector can be reconstructed to the original space. See again, Principal Component Neural Networks: Theory and Applications, cited earlier.

This mapping can be used to reduce the original vectors, which may involve several thousand dimensions, to a concept-space representation in only several dozen dimensions. For example, if an MRI and ACL reconstruction and physical therapy tend to commonly co-occur, then it is expected that the reduced-space representation, while possibly losing information regarding the precise services performed, would indicate that there is a serious knee injury requiring orthopedic surgery. Indeed, one might expect that each of the individual service-codes for MRI, ACL reconstruction and physical therapy maps to a sinMilar point in the concept-space; at the very least, the presence of one service-code, by dimensionality reduction and then reconstruction, would suggest the possible occurrence of the others. Furthermore, the more consistency in the starting vector, the better the reconstruction that can be expected.

There is an important benefit to this compact representation, beyond the memory savings and computational efficiencies. Using this methodology it is possible to get at the inherent essence of what is really happening, washing away specific details that may differ. In a sense, the noise in the service-code vector is removed, leaving behind clean signals for further analyses; it can also be said that the list of specific service codes has been mapped to a summarization of the types of illnesses associated with the patient.

Using this Representation

The methodology described above takes any set of service-codes and converts it into a fixed-dimensional representation characterizing the individual (patient, provider, provider/patient entity, etc.), such that similar individuals map to similar points in the vector space. This representation can be used to assess consistency of services. The following three somewhat different scenarios illustrate this capability:

1. Internal Consistency: Suppose one wishes to look at the internal consistency of an individual's set of service-codes; the individual here can be the patient, for example. That is, do these service codes typically co-occur? A solution is to map down to the reduced-space, and then attempt to reconstruct back to the original space. The more consistent the set of services, the closer this reconstructed vector should be to the original; conversely, the poorer the reconstruction, the less consistent the set of service-codes. Patients whose reconstructed vectors are significantly different from their original vectors are having inconsistent services provided to them. This may suggest that the patient is engaged in fraudulent conduct, or that the providers of some of the services are. The inconsistent portion of the services may be identified, for example, as those that are unusual for the diagnosis of the patient. Examples of measures of reconstruction quality (between original and reconstructed vector) include Euclidean distance, dot-product, etc.

2. Inference/Interacting-Entities: Suppose one wishes to examine how consistent a provider's activity is on a client. The provider/client set of services (i.e., the set of services provided by a specific provider on a specific client) may not be expected to map to a nearly identical representation as that of the remaining set of services associated with the client, as the provider's activity may be consistent with a subset of services that corresponds to a given provider specialty. However, it would be expected that the provider/client services could be reasonably inferred as consistent based on everything else associated with the client.

For example, in one embodiment, the claim data for a client's activity, excluding the provider in question, is used to map the services provided to the client to the reduced space and then reconstructed back to the original service-code space, as described above with reference to the compression network and SVD-based PCA. The reduced-space representation provides a clinical summary of the client in terms of services the client is experiencing, and the reconstruction indicates what services are associated with that type of clinical situation. For each service-code performed by the provider in question on the client, it can be assessed whether it is reasonable based on the value for the service code in the client's associated reconstructed component; in other words, is it more likely than average to see the service-codes performed by the provider in question based on the other known activity on the client? An overall consistency measure can be calculated for the service codes for the provider in question with respect to the service codes in the client's reconstructed service code vector.

An alternative approach is to use the technique of the internal consistency scenario just described, but run twice. First, internal consistency on the client's activity is assessed, excluding services associated with the provider in question; second, internal consistency on the client's entire set of activity is assessed, including the provider's set of services. A decrease, from the first to the second assessment, in the level of internal consistency provides a measure of inconsistency in the provider's servicing of the client, since it shows that when the provider's services are included, the overall consistency of the client's reconstructed vector decreases.

3. Multiple Coding Schemes: Suppose that there are two or more different types of codes, such as ICD9 diagnosis codes and CPT procedure codes, and it is desirable to see if the two sets correspond, for example, to see that the procedures being performed are consistent with the diagnosis. Consider the original service-code vector to have components corresponding to each set of codes.

One approach is to employ the technique of scenario 1 on the entire vector. A second approach is to first zero out the components associated with one of the code-types in the original service-code activity vector, and use the methodology of scenario 2 to assess if those services could be reasonably inferred. This can then be repeated for the other code-type(s).

Alternatively, each of the vectors with the components of one of the code-types zeroed can be mapped out to the reduced space, and the distances between the reduced-space representations evaluated. Again, any reasonable measure of proximity, such as Euclidean distance, dot-product, etc. can be used. The Medicare example presented next uses this methodology.

Those of skill in the art will recognize that variations and combinations of the above methodologies are possible, and can be chosen based upon the desired analysis best suited to the particular application.

Figure 6:
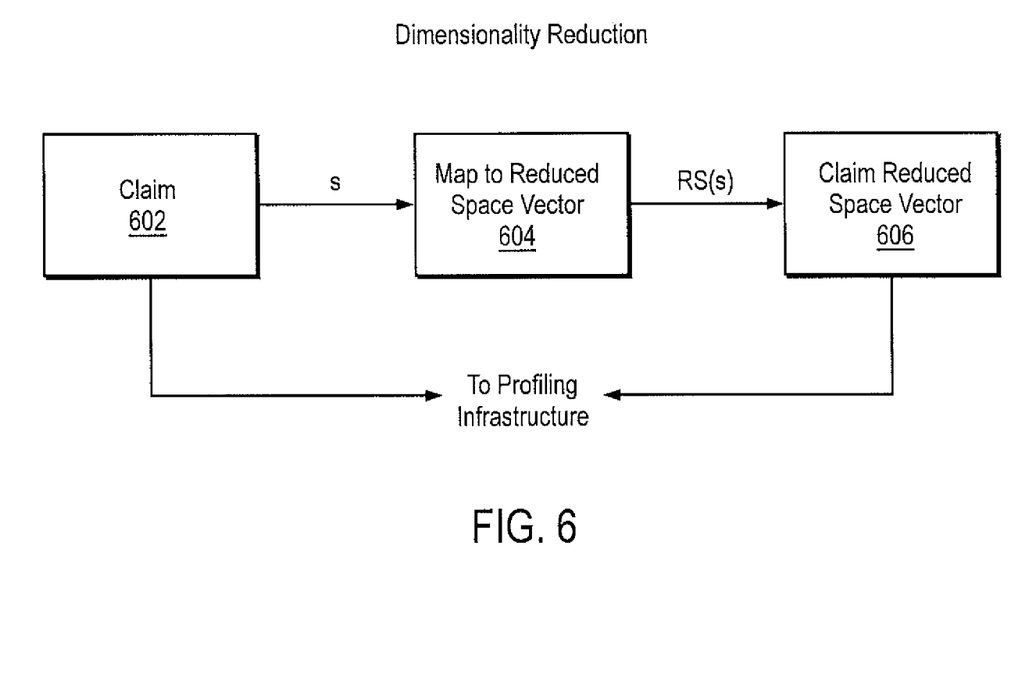
FIG. 6 is a flowgraph of the dimensionality reduction analysis methodology in accordance with an embodiment of the present invention.

Thus, referring now to FIG. 6, incoming claims 602 are mapped 604 as described above to a reduced space vector representation 606. This reduced space vector representation 606 is then an input, along with the claim itself 602, to the profiling infrastructure described above.

An Example: Analyzing Medicare Activity

One application of an embodiment of the present invention is a client-centric analysis of the consistency, or lack thereof, of a client's Medicare Part A and Part B claims. Medicare Part A covers care in hospitals as an inpatient, critical access hospitals, skilled nursing facilities, hospice care, and some home healthcare. Medicare Part B covers doctors' services, outpatient hospital care, and some other medical services that Part A does not cover, such as the services of physical and occupational therapists, and some home health services. Part B claims correspond to an individual (typically a physician) provider; Part B services are represented by CPT and HCPCS codes. Part A claims are associated with facilities, and each facility type has its own coding scheme; skilled-nursing-facilities use RUG codes, while inpatient facilities denote services by MDC category.

For each client, an inconsistency metric ranging from −1 (most consistent) to +1 (most inconsistent) can be calculated, based on that client's utilization patterns. In fact, two separate sets of inconsistency metrics are calculated, one which takes into account all activity through the year, and one which focuses on activity within an episode of care. Three pair-wise inconsistency metrics are determined, depending on the activity the client has experienced: PartB-vs-MDC inconsistency, RUG-vs-MDC, and PartB-vs-RUG inconsistency. The LSA-inspired approach is used here to provide a holistic comparison for each client. The methodology of the third scenario in the previous section is employed, namely to map each service-code subset (grouping service-codes associated with a given coding scheme) to a reduced space and compare the resulting vectors.

Figure 7:
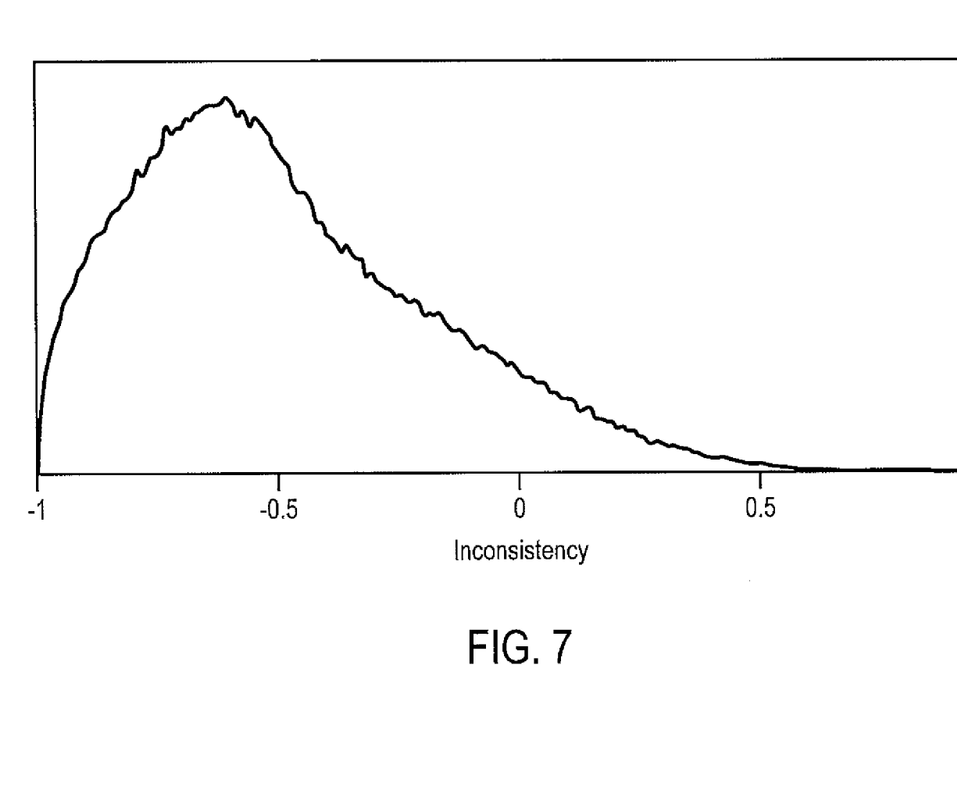
FIG. 7 illustrates a distribution of the PartB-vs-MDC (i.e. physician versus inpatient facility) inconsistency metric in accordance with an embodiment of the present invention.

FIG. 7 illustrates the distribution of the PartB-vs-MDC (i.e. physician versus inpatient facility) inconsistency metric, with the vertical axis representing fractions of claims. Note that most clients have a very consistent mix of Part B and MDC activity. The right skew of this distribution makes the measure quite useful for outlier detection. This distribution is typical of inconsistency distributions used in this model.

A facility that has an unusually high number of clients with inconsistent activity may be doing something fraudulent or abusive. In one embodiment/the present invention rolls-up the inherent inconsistency of each client's activity to the provider level, for example as the average measure of inconsistency for the provider based on the inconsistency measures for all of its clients. Since the inconsistency metric is calculated at the client level, clients provide the key to fraud and can serve as the focus of any investigation based on the inconsistency model. By examining the mix of RUGS, MDCs, and PartB procedures on individual clients, unusual patterns of utilization can be detected.

Implementation

Each of the three consistency approaches described above can be implemented in a real-time/recursive-update mode, incrementally updating profiles as transactions come in:

The repeat-services approach simply involves tracking the most recent client/service-code activity, across client/service-code pairs.

The pair-wise approach involves updating the overall consistency measure in light of the new service code s1, that is to calculate C(s1,S2). Services associated with the entity S2 (e.g. client) are stored.

In the LSA-inspired approach, a reduced-space representation of service-code activity can be maintained for each of the relevant entities in the system (e.g. provider/client, client, etc.). When a new transaction enters the system, because the PCA-based mapping is linear (matrix multiplication), the existing reduced-space representation can simply be updated by adding in the reduced-space representation of the new service-code.

In one embodiment, updating occurs so that each historical claim has equal weight. In an alternative embodiment/a decaying mechanism is used so that more recent activity takes precedence over older activity.

Reason-Codes

When generating a fraud-risk score for an entity that is made up of many transactions, it is important to have reason-codes that provide an indication as to what particular activity is most suspicious. Whether fraud-risk is being assessed at the claim level, provider/client level, or rolling-up to the provider-level, each of the embodiments presented lends itself to focusing attention on the activity that is most suspect.

Repeat-service: In one embodiment, each individual claim has a risk-score associated with it (in particular, the table look-up value). Whatever entity the claims are rolled up to, attention can be focused on the most suspect activity by working backwards. For example, a given provider's claims having the highest risk-score can be identified. In the cascaded profiling environment, attention may be restricted to claims associated with, e.g., provider/client pairs that appear most suspicious for the provider.

Pair-wise Co-occurrence: A risk-score can similarly be associated with a transaction with service-code s1, namely c(s1,S2), using the notation described earlier. The discussion above regarding repeat-services then applies. The subset of S2 that is most inconsistent with s1 can also be identified.

Vector-based Dimensionality reduction: Any vector that has been projected onto the reduced-space can be mapped back to the original space. There is information loss in the original projection to the lower dimensional space, so the reconstructed vector does not exactly match the starting vector. If the internal consistency of single set of service-codes is being examined, then the service-code signals in the reconstructed vector that most mis-match the corresponding value in the original vector are identified. If comparing two different sets of service-codes, then one of the vectors is reduced and reconstructed to see which service-codes present in the other seem most unlikely.

Absence of Activity

This description has so far been focused on assessing how unusual it is for certain activity to be present. It is also possible to assess how unusual it is for certain activity to be absent. For example, if a client has orthopedic surgery, the operation could be expected to be preceded by some radiology activity (e.g. an X-ray or MRI).

Repeat-service: For each service-code previously occurring on an entity, use the same look-up table to assess how unlikely it is for the service not to have been repeated since the most recent activity.

Pair-wise Co-occurrence: For each service-code, use the same pair-wise statistics to identify other procedures that are likely to occur but do not.

Vector-based Dimensionality reduction: As described above, the present invention analyzes which service-codes that do occur would not, based on the reduction and reconstruction of an activity-vector, be reasonably inferred. In a similar manner, the present invention can assess if service-codes that are inferred are actually not present. Uses of the Reduced-Space (LSA-inspired) Representation While the reduced-space representation has been described as a method of uncovering inconsistent activity, this representation offers additional uses as well:

Clustering: Individuals with similar reduced-space representations are themselves similar. Clustering the data, using the reduced-space representation to characterize each individual, creates peer groups. This can be used to determine patients with similar illnesses and patterns of care, providers with similar practices or specialties, etc.

Predictive Modeling: This reduced-space representation can act as a set of input variables to predict or forecast other items of interest, such as expected utilization of services, provider specialty, etc.

Behavior Change: Sharp changes in service-mix can be detected by comparing short-term and long-term reduced-space representations of service-code activity. Such a change may suggest a change in a provider's servicing pattern, the onset of fraud/abuse, etc.

The algorithms and displays presented herein are not inherently related to any particular computer or other apparatus. Various general-purpose systems may also be used with programs in accordance with the teachings herein, or it may prove convenient to construct more specialized apparatus to perform the required method steps. In addition, the present invention is not described with reference to any particular programming language. A variety of programming languages may be used to implement the teachings of the present invention as described herein, and any references to specific languages are provided for disclosure of enablement and best mode of the present invention.

The present invention is well suited to a wide variety of computer network systems over numerous topologies. Within this field, the configuration and management of large networks comprise storage devices and computers that are communicatively coupled to dissimilar computers and storage devices over a network, such as the Internet.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

What is claimed is:

1. A method for detecting fraud in health care transactions, the method being implemented by one or more data processors and comprising:

receiving, by at least one data processor, a transaction record, the transaction record characterizing at least one service provided to a client by a provider on a date;

for each service in the transaction record:
determining, by at least one data processor, a time interval between the date the service was provided to the client, and a date the same service was previously provided to the client;
determining, by at least one data processor, a likelihood for the service to be repeated given the time interval using co-occurrence data based on a vector space modeling of historical service co-occurrence in which performed service codes are represented in a vector space derived from a statistical distribution of service codes in reimbursement claims; and responsive to the likelihood exceeding a first threshold, indicating, by at least one data processor, that the transaction is potentially fraudulent.

2. The method of claim 1 further comprising:
responsive to the likelihood not exceeding the threshold, indicating, by at least one data processor, that the transaction is not fraudulent.

3. The method of claim 1, further comprising:
for each provider, maintaining, by at least one data processor, a metric of all determined likelihood values for instances of the service provided by the provider; and
responsive to the metric exceeding a second threshold, indicating, by at least one data processor, that the provider should be investigated for fraud.

4. The method of claim 1, further comprising:
for each provider, maintaining, by at least one data processor, a metric of all determined likelihood values for each service provided by the provider; and
responsive to the metric exceeding a second threshold, indicating, by at least one data processor, that the provider should be investigated for fraud.

5. The method of claim 1, wherein determining the likelihood for the service to be repeated given the time interval further comprises:
for each of a plurality of time intervals, using, by at least one data processor, historical data from a plurality of transactions to determine a likelihood with which the service is repeated during the interval.

6. A method for implementation by one or more data processors and comprising:
receiving, by at least one data processor, data characterizing a plurality of health care transactions, each transaction including at least one service provided to a client by a provider;
retrieving, by at least one data processor, co-occurrence data, the co-occurrence data indicating an historical likelihood that a client will receive both a first service and a second service, the co-occurrence data being based on a vector space modeling of historical service co-occurrence in which performed service codes are represented in a vector space derived from the statistical distribution of service codes in reimbursement claims;
retrieving, by at least one data processor, client historical data, the historical data including a plurality of historical services received by the client;
for each of the plurality of historical services in the client historical data, determining, by at least one data processor, from the co-occurrence data a likelihood of the provided service co-occurring with the historical service in order to determine an overall inconsistency metric; and
responsive to the overall inconsistency metric exceeding a threshold, indicating, by at least one data processor, that the transaction is potentially fraudulent.

7. The method of claim 6, wherein determining the likelihood of the provided service co-occurring with the historical service in order to determine the overall inconsistency metric further comprises:
determining, by at least one data processor for each combination of the provided service and a historical service received by the client, an inconsistency value; and
determining, by at least one data processor, a metric of the inconsistency values.

8. The method of claim 6 wherein services provided to the client by the provider are excluded from the client historical data used to determine the overall inconsistency metric.

9. A system for detecting fraud in health care transactions comprising:
at least one data processor; and
memory coupled to the at least one data processor, the memory storing instructions, which when executed, cause the at least one processor to perform operations comprising:
receiving a transaction record;
for each service in the transaction record, the transaction record characterizing at least one service provided to a client by a provider on a date:
determining a time interval between the date the service was provided to the client, and a date the same service was previously provided to the client;
determining a likelihood for the service to be repeated given the time interval using co-occurrence data based on a vector space modeling of historical service co-occurrence in which performed service codes are represented in a vector space derived from a statistical distribution of service codes in reimbursement claims; and
responsive to the likelihood exceeding a first threshold, indicating that the transaction is potentially fraudulent.

10. The system of claim 9, wherein the operations further comprise:
responsive to the likelihood not exceeding the threshold, indicating that the transaction is not fraudulent.

11. The system of claim 9, wherein the operations further comprise:
for each provider, maintaining a metric of all determined likelihood values for instances of the service provided by the provider; and
responsive to the metric exceeding a second threshold, indicating that the provider should be investigated for fraud.

12. The system of claim 9, wherein the operations further comprise:
for each provider, maintaining a metric of all determined likelihood values for each service provided by the provider; and
responsive to the metric exceeding a second threshold, indicating that the provider should be investigated for fraud.

13. The system of claim 9, wherein determining the likelihood for the service to be repeated given the time interval further comprises:
for each of a plurality of time intervals, using historical data from a plurality of transactions to determine a likelihood with which the service is repeated during the interval.

14. A system for detecting fraud in health care transactions, each transaction including at least one service provided to a client by a provider, the system comprising:
at least one data processor; and
memory coupled to the at least one data processor, the memory storing instructions, which when executed, cause the at least one processor to perform operations comprising:
retrieving co-occurrence data, the co-occurrence data indicating an historical likelihood that a client will receive both a first service and a second service, the co-occurrence data being based on a vector space modeling of historical service co-occurrence in which performed service codes are represented in a vector space derived from a statistical distribution of service codes in reimbursement claims;

retrieving client historical data, the historical data including a plurality of historical services received by the client;

for each of the plurality of historical services in the client historical data, determining from the co-occurrence data a likelihood of the provided service co-occurring with the historical service in order to determine an overall inconsistency metric; and responsive to the overall inconsistency metric exceeding a threshold, indicating that the transaction is potentially fraudulent.

15. The system of claim 14, wherein determining the likelihood of the provided service co-occurring with the historical service in order to determine the overall inconsistency metric further comprises:

determining for each combination of the provided service and a historical service received by the client, an inconsistency value; and determining a metric of the inconsistency values.

16. The system of claim 15 wherein services provided to the client by the provider are excluded from the client historical data used to determine the overall inconsistency metric.

17. A method for implementation by at one or more data processors comprising:

retrieving, by at least one data processor, co-occurrence data indicating an historical likelihood that a client will receive both a first service and a second service, the co-occurrence data being based on a vector space modeling of historical service co-occurrence in which performed service codes are represented in a vector space derived from a statistical distribution of service codes in reimbursement claims;

retrieving, by at least one data processor, client historical data, the historical data including a plurality of historical services received by the client;

for each of the plurality of historical services in the client historical data, determining, by at least one data processor, from the co-occurrence data a likelihood of the provided service co-occurring with the historical service in order to determine an overall inconsistency metric; and responsive to the overall inconsistency metric exceeding a threshold, indicating, by at least one data processor, that the transaction is potentially fraudulent.

18. The method as in claim 17, wherein determining the likelihood of the provided service co-occurring with the historical service in order to determine the overall inconsistency metric further comprises:

determining, by at least one data processor, for each combination of the provided service and a historical service received by the client, an inconsistency value; and determining, by at least one data processor, a metric of the inconsistency values.

19. The method of claim 18 wherein services provided to the client by the provider are excluded from the client historical data used to determine the overall inconsistency metric.

20. A non-transitory computer program product storing instructions, which when executed by at least one data processor, result in operations comprising:

retrieving, by the at least one data processor, co-occurrence data indicating an historical likelihood that a client will receive both a first service and a second service, the co-occurrence data being based on a vector space modeling of historical service co-occurrence in which performed service codes are represented in a vector space derived from a statistical distribution of service codes in reimbursement claims;

retrieving, by the at least one data processor, client historical data, the historical data including a plurality of historical services received by the client;

for each of the plurality of historical services in the client historical data, determining, by the at least one data processor, from the co-occurrence data a likelihood of the provided service co-occurring with the historical service in order to determine an overall inconsistency metric; and responsive to the overall inconsistency metric exceeding a threshold, indicating, by the at least one data processor, that the transaction is potentially fraudulent.

21. The computer program product as in claim 20, wherein determining the likelihood of the provided service co-occurring with the historical service in order to determine the overall inconsistency metric further comprises:

determining, by the at least one data processor, for each combination of the provided service and a historical service received by the client, an inconsistency value; and determining, by the at least one data processor, a metric of the inconsistency values.

22. The computer program product of claim 21 wherein services provided to the client by the provider are excluded from the client historical data used to determine the overall inconsistency metric.

* * * * *